US009166171B2

(12) United States Patent
Ohno et al.

(10) Patent No.: US 9,166,171 B2
(45) Date of Patent: Oct. 20, 2015

(54) METHANOFULLERENE DERIVATIVES AND PHOTOELECTRIC CONVERSION DEVICES USING SAME

(75) Inventors: Toshinobu Ohno, Osaka (JP); Yuko Takao, Osaka (JP); Kazuyuki Moriwaki, Osaka (JP); Fukashi Matsumoto, Osaka (JP); Souichi Uchida, Tokyo (JP); Satoru Ikeda, Tokyo (JP)

(73) Assignees: Osaka Municipal Technical Research Institute, Osaka-shi, Osaka (JP); JX Nippon Oil & Energy Corporation, Tokyo (JP)

( * ) Notice: Subject to any disclaimer, the term of this patent is extended or adjusted under 35 U.S.C. 154(b) by 716 days.

(21) Appl. No.: 13/386,580

(22) PCT Filed: Jun. 25, 2010

(86) PCT No.: PCT/JP2010/060844

§ 371 (c)(1), (2), (4) Date: Jan. 23, 2012

(87) PCT Pub. No.: WO2011/010526

PCT Pub. Date: Jan. 27, 2011

(65) Prior Publication Data

US 2012/0123058 A1 May 17, 2012

(30) Foreign Application Priority Data

Jul. 24, 2009 (JP) ................................ 2009-172908

(51) Int. Cl.

| | |
|---|---|
| ***H01L 51/46*** | (2006.01) |
| ***H01L 51/30*** | (2006.01) |
| ***H01L 51/00*** | (2006.01) |
| ***B82Y 10/00*** | (2011.01) |
| ***C07C 13/68*** | (2006.01) |
| ***C07D 333/08*** | (2006.01) |
| ***C07D 333/24*** | (2006.01) |
| *H01L 51/42* | (2006.01) |

(52) U.S. Cl.

CPC ............. *H01L 51/0047* (2013.01); *B82Y 10/00* (2013.01); *C07C 13/68* (2013.01); *C07D 333/08* (2013.01); *C07D 333/24* (2013.01); *C07C 2104/00* (2013.01); *H01L 51/0036* (2013.01); *H01L 51/4253* (2013.01); *Y02E 10/549* (2013.01)

(58) Field of Classification Search

CPC ....... H01B 1/02; H01L 51/0046; B82Y 30/00

USPC .................. 252/500–519.1; 136/263; 257/40; 526/257

See application file for complete search history.

(56) References Cited

U.S. PATENT DOCUMENTS 5,331,183 A 7/1994 Sariciftci et al.

FOREIGN PATENT DOCUMENTS

| | | | |
|---|---|---|---|
| EP | 0647606 | A1 * | 10/1994 |
| EP | 2239797 | A1 | 10/2010 |
| JP | 2009-057356 | A | 3/2009 |
| JP | 2009-196965 | A | 9/2009 |
| WO | 2008006071 | A2 | 1/2008 |
| WO | 2009087948 | A1 | 7/2009 |

OTHER PUBLICATIONS

Zheng ("Methanofullerenes Used as Electron Acceptors in Polymer Photovoltaic Devices." JPC B, 108, pp. 11921-11926, 2004).*

Int'l Search Report issued Aug. 10, 2010 in Int'l Application No. PCT/JP2010/060844.

Mayorova et al, "Synthesis and investigation of fullerene-based acceptor materials," Mendeleev Communications, vol. 17, pp. 175-177 (2007).

Zhang et al, "A Simple and Effective Way of Achieving Highly Efficient and Thermally Stable Bulk-Heterojunction Polymer Solar Cells Using Amorphous Fullerene Derivatives as Electron Acceptor," Chemistry of Materials, vol. 21, No. 13, pp. 2598-2600 (2009).

Kitamura et al, "Stereoelectronic Effects in Diastereoselective Formation of Fulleroids," Organic Letters, vol. 9, No. 20, pp. 4045-4048 (2007).

Tada et al, "Synthesis and Reactions of 2,2-[60]Fullerenoalkanoyl Chlorides," The Journal of Organic Chemistry, vol. 71, No. 4, pp. 1633-1639 (2006).

(Continued)

*Primary Examiner* — Tri V Nguyen

(74) *Attorney, Agent, or Firm* — Panitch Schwarze Belisario & Nadel LLP

(57) ABSTRACT

The present invention provides a novel methanofullerene derivative applicable as an organic semiconductor material in electronics devices such as organic FETs and electroluminescence devices and solar cells, represented by formula (I) wherein the average value of $^{13}$C-NMR chemical shift values of carbons $C_2$ and $C_{2'}$ on FL, bonded to $C_1$ is 80.10 ppm or greater, (I)

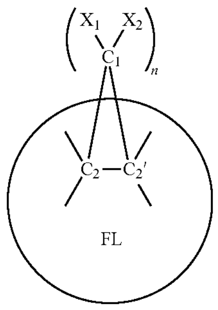

wherein FL represents fullerenes, X1 and X2 are each an aromatic hydrocarbon, an alkyl group or the like, $C_2$ and $C_{2'}$ are carbon atoms on FL, bonded to $C_1$, and n is an integer of 1 to 10.

3 Claims, No Drawings

(56) References Cited

OTHER PUBLICATIONS

Yang et al, "Thinner-film plastic photovoltaic cells based on different C60 derivatives," Polymers for Advanced Technologies, vol. 17, pp. 500-505 (2006).
Troshin et al, "Self-Assembly of Thiophene- and Furan-Appended Methanofullerenes with Poly(3-Hexylthiophene) in Organic Solar Cells," ChemSusChem, vol. 3, pp. 356-366 (2010).
Sariciftci et al, "Photoinduced Electron Transfer from a Conducting Polymer to Buckminsterfullerene," Science, New Series, vol. 258, No. 5087, pp. 1474-1476 (1992).
Brabec et al, "Photovoltaic properties of conjugated polymer/methanofullerene composites embedded in a polystyrene matrix," Journal of Applied Physics, vol. 85, No. 9, pp. 6866-6872 (1999).
Padinger et al, "Effects of Postproduction Treatment on Plastic Solar Cells," Advanced Functional Materials, vol. 13, No. 1, pp. 85-88 (2003).
Reyes-Reyes et al, "High-efficiency photovoltaic devices based on annealed poly(3-hexylthiophene) and 1-(3-methoxylcarbonyl)-propyl-1-phenyl-(6,6)C61 blends," Applied Physics Letters, vol. 87, No. 083506, pp. 1-3 (2005).
Ma et al, "Thermally Stable, Efficient Polymer Solar Cells with Nanoscale Control of the Interpenetrating Network Morphology," Advanced Functional Materials, vol. 15, pp. 1617-1622 (2005).
Kooistra et al, "Increasing the Open Circuit Voltage of Bulk-Heterojunction Solar Cells by Raising the LUMO Level of the Acceptor," Organic Letters, vol. 9, No. 4, pp. 551-554 (2007).
Extended European Search Report issued Feb. 18, 2014 in EP Application No. 10802147.8.
Troshin et al, "Material solubility-photovoltaic performance relationship in the design of novel fullerence derivatives for bulk heterojunction solar cells," Advanced Functional Matericals, vol. 19, No. 5, pp. 779-788 (Mar. 2009).
Mayorova et al, "Electronic supplementary materials—Mendeleev Commun: Synthesis and investigation of fullerene-based acceptor materials," retrieved from the internet at http://www.sciencedirect.com/science/MiamiMultiMediaURL/1-s2.0-S095994360700079XFULL/S095994360700079X-mmc1.pdf/273605/FULL/S095994360700079X/6cea6f6b401240e807bfe54151a6748d/mmc1.pdf (Jun. 2007).

* cited by examiner

METHANOFULLERENE DERIVATIVES AND PHOTOELECTRIC CONVERSION DEVICES USING SAME

CROSS-REFERENCE TO RELATED APPLICATION

This application is a Section 371 of International Application No. PCT/JP2010/060844, filed Jun. 25, 2010, which was published in the Japanese language on Jan. 27, 2011, under International Publication No. WO 2011/010526 A1, and the disclosure of which is incorporated herein by reference.

TECHNICAL FIELD

The present invention relates to methanofullerene derivatives. The methanofullerene derivatives of the present invention are materials applicable as organic semiconductor materials in electronics devices such as organic field-effect transistors (organic FET) and electroluminescence devices and solar cells, and the present invention also relates to photoelectric conversion devices using these methanofullerene derivatives.

BACKGROUND ART

Solar power generation, which converts light energy such as sunlight to electric energy is an extremely clean way to generate electricity because it is not accompanied with $CO_2$ emission, and has been expected solve the global warming issues by reducing greenhouse gas emissions. An organic thin film solar cell can be expected to be large in area, and produced by a simple and inexpensive manner and thus is deemed a promising next generation solar cell because of its light weight and great flexibility. However, a significant increase in the conversion efficiency of the organic thin film solar cell has become an important issue towards the practical use of the cell.

In 1992 Sariciftci demonstrated that a hetero junction cell of an electrically conductive polymer that is a hole transport material and fullerene $C_{60}$ can provide an efficient charge separation (see Non-Patent Literature 1, Patent Literature 1).

Furthermore, for the purpose of enhancing the compatibility of a fullerene with a hole transport material, a methanofullerene was synthesized, wherein phenyl and butyric acid ester group are cross-linked via methylene (phenyl-$C_{61}$-butyric acid methyl ester: PCBM). When poly[2-methoxy,5-(2'-ethyl-hexyloxy)-p-penylene vinylene] (MEH-PPV) wherein an alkoxy group is introduced in poly p-phenylene vinylene is mixed with PCBM to form an active layer, the resulting MEH-PPV/PCBM system with this active layer was significantly improved in photo conversion efficiency as compared with $C_{60}$ (see Non-Patent Literature 2).

Sariciftci et al has accomplished an energy conversion efficiency of 3.5 percent with a bulk-hetero junction structure comprising a mixed active layer of a conjugated polymer such as poly(3-hexylthiophene), P3HT that is a hole transport material and a methanofullerene derivative PCBM (see Non-Patent Literature 3).

Heeger and Carroll et al each have reported that an energy conversion efficiency of approximately 5 percent was accomplished by heating this blend film device (see Non-Patent Literatures 4 and 5).

In order to promote an significant improvement in energy conversion efficiency, it is now important to develop novel p-type semiconductor materials and n-type semiconductor materials. P3HT and PCBM are now standard materials for a p-type semiconductor and an n-type conductor, respectively to manufacture a device, and thus the conversion efficiency has been currently enhanced only by improving the device. Although it has been reported that some new polymers are useful for the p-type semiconductor, there are only few examples of development of fullerene derivatives for the n-type semiconductor used in a photoelectric conversion material, and thus it is no exaggeration to say that there is nothing to beyond PCBM.

When a consideration is now given to the design guideline of a fullerene derivative, the compatibility of the fullerene derivative with a hole transport material is extremely important as apparent from the fact that PCBM was synthesized for the purpose of enhancing the compatibility of a fullerene with a hole transport material to produce a donor/acceptor complex film, and the MEH-PPV/PCBM system was significantly improved in photoelectric conversion efficiency as compared with $C_{60}$. It has been also reported that substitution of the phenyl ring of PCBM with an electron-donating substituent increases LUMO (lowest unoccupied molecular orbital, the orbital with the lowest energy among the molecular orbital unoccupied with electrons), and when the PCBM with the substituent is fabricated into a device, it can increase the open end voltage, resulting in an increase in energy conversion efficiency (Non-Patent Literature 6).

Under these circumstances, the molecular design of fullerene derivatives has been demanded, which are excellent in dissolubility, enhanced in compatibility with polymers that are p-type semiconductors, and have a high open end voltage.

The inventors of the present invention proposed a novel methanofullerene derivative to satisfy these demands (Patent Literature 2) but it is not sufficient in open end voltage. A methanofullerene derivative with a higher open end voltage has been demanded.

CITATION LIST

Patent Literature

Patent Literature 1: U.S. Pat. No. 5,331,183

Patent Literature 2: Japanese Laid-Open Publication No. 2009-57356

Non Patent Literature

Non Patent Literature 1: "Science" vol. 258, pp. 1474-1476, 1992, by N. S. Sariciftci, L. Smilowitz, A. J. Heeger, F. Wudl Non Patent Literature 2: "Journal of Applied Physics", vol. 85, p. 6866, 1999, by C. J. Brabec, F. Padinger, N. S. Sariciftci, J. C. Hummelen Non Patent Literature 3: "Advanced Functional Material", vol. 13-1, pp. 85-88, 2003, by F. Padinger, R. S. Rittberger, N. S. Sariciftci, Non Patent Literature 4: "Applied Physics Letters", vol. 87, 083506, 2005, by M. R-Reyes, K. Kim, D. L. Carroll, Non Patent Literature 5: "Advanced Functional Material", vol. 15, pp. 1617-1622, 2005, by W. Ma, C. Yang, X. Gong, K. Lee, A. J. Heeger Non Patent Literature 6: "Organic Letters", vol. 9, pp. 551-554, 2007, by F. B. Kooistra, J. Knol, F. Kastenberg, L. M. Popescu, W. J. H. Verhees, J. M. Kroon, J. C. Hummelen

SUMMARY OF INVENTION

Technical Problem

As the results of the extensive studies conducted by the inventors in view of the above-described problems, they have succeeded in developing a methanofullerene derivative that is high in dissolubility and LUMO, by conducting a molecular design in which electron attractive groups such as ester and the like are removed from PCBM.

Solution to Problem

That is, the present invention relates to a methanofullerene derivative represented by formula (I) wherein the average value of $^{13}$C-NMR chemical shift values of carbons $C_2$ and $C_{2'}$ on FL, bonded to $C_1$ is 80.10 ppm or greater, (I)

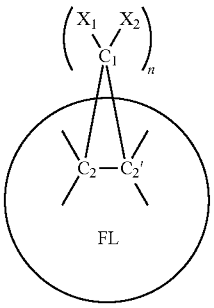

wherein FL represents fullerenes, $X_1$ and $X_2$ are each (a) a monovalent group derived from aromatic hydrocarbons, polycyclic aromatic hydrocarbons, heteroaromatic hydrocarbons containing a heteroatom in the skeleton, or polycyclic heteroaromatic hydrocarbons, (b) a monovalent group derived from aromatic hydrocarbons, polycyclic aromatic hydrocarbons, heteroaromatic hydrocarbons containing a heteroatom in the skeleton, or polycyclic heteroaromatic hydrocarbons, having halogen, or an alkyl, alkoxy, alkyithio or aryl group, substituted for at least one of the hydrogen atoms, (c) a monovalent group derived from oligomers of up to 30-mer of aromatic hydrocarbons, polycyclic aromatic hydrocarbons, heteroaromatic hydrocarbons containing a heteroatom in the skeleton, or polycyclic heteroaromatic hydrocarbons, or (d) a group selected from alkyl, alkoxy, alkoxyalkyl, alkylthio and alkylthioalkyl groups, FL is bonded to $X_1$ and $X_2$ via methine carbon $C_1$, $C_2$ and $C_{2'}$ are carbon atoms on FL, bonded to $C_1$, and n is an integer of 1 to 10.

The present invention also relates to the foregoing fullerene derivative represented by formula (I) wherein $X_1$ in formula (I) is a monovalent group derived from aromatic rings or thiophene rings represented by formula (II), (II)

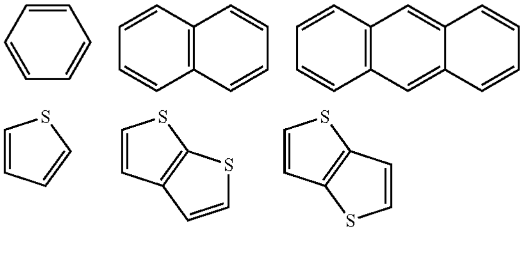

-continued

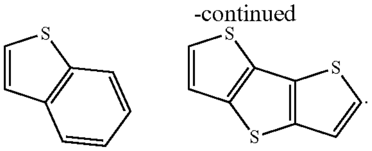

The present invention also relates to the foregoing methanofullerene derivative wherein $X_2$ in formula (I) is an alkyl, alkoxy, alkoxyalkyl, alkyythio, or alkylthioalkyl group.

The present invention also relates to a photoelectric conversion device comprising the foregoing methanofullerene derivative as an electron transport material.

The present invention also relates to the foregoing photoelectric conversion device comprising a conjugated polymer compound containing a thiophen ring as a hole transport material.

Advantageous Effects of Invention

The present invention provides a methanofullerene derivative that is enhanced in dissolubility, compatibility with polymers and open end voltage and excellent in charge mobility and charge separation ability, and the use of such a methanofullerene derivative leads to a photoelectric conversion device that is excellent in electron properties and durability.

The novel methanofullerene derivative of the present invention is an organic semiconductor material that is applicable to electronics devices such as organic FETs, electroluminescence devices or the like.

DESCRIPTION OF EMBODIMENTS

The methanofullerene derivative of the present invention will be described in detail below.

The methanofullerene derivative of the present invention is a compound represented by formula (I) below and has a structure wherein $C_2$ and $C_{2'}$ on the fullerene cross-links with $C_1$ bonded to $X_1$ and $X_2$.

(I)

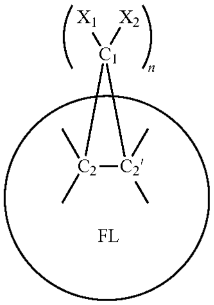

In formula (I), the encircled FL indicates fullerenes. The term "fullerenes" is a collective term of compounds having a three-dimensional closed shell nucleolus structure wherein the carbon atoms of Sp2 type are spherically bonded to each other. Specific examples of such a compound include fullerene, derivatives thereof, and those including metal atoms or compounds in their skeletons. Specific examples include those represented by chemical formulas such as $C_{60}$, $C_{70}$, $C_{76}$, $C_{78}$, $C_{82}$, $C_{84}$, $C_{90}$, and $C_{96}$. Among these, preferred are $C_{60}$ and $C_{70}$.

In formula (I), $X_1$ and $X_2$ are each (a) a monovalent group derived from aromatic hydrocarbons, polycyclic aromatic hydrocarbons, heteroaromatic hydrocarbons containing a heteroatom in the skeleton, or polycyclic heteroaromatic hydrocarbons, (b) a monovalent group derived from aromatic hydrocarbons, polycyclic aromatic hydrocarbons, heteroaromatic hydrocarbons containing a heteroatom in the skeleton, or polycyclic heteroaromatic hydrocarbons, having halogen, or an alkyl, alkoxy, alkyithio or aryl group, substituted for at least one of the hydrogen atoms, (c) a monovalent group derived from oligomers of up to 30-mer of aromatic hydrocarbons, polycyclic aromatic hydrocarbons, heteroaromatic hydrocarbons containing a heteroatom in the skeleton, or polycyclic heteroaromatic hydrocarbons, or (d) a group selected from alkyl, alkoxy, alkoxyalkyl, alkylthio and alkylthioalkyl groups.

The aromatic hydrocarbons and polycyclic aromatic hydrocarbons are preferably those having 6 to 30 carbon atoms, such as benzene, naphthalene, and anthracene.

The heteroaromatic hydrocarbons and polycyclic heteroaromatic hydrocarbons are preferably those having 6 to 30 carbon atoms. The heteroatom is preferably sulfur. Examples include thiophene-based hoetroaromatic compounds such as thiophene, benzothiophene, and thienothiophene.

Examples of the aromatic hydrocarbons, polycyclic aromatic hydrocarbons, heteroaromatic hydrocarbons and polycyclic heteroaromatic hydrocarbons include compounds having aromatic rings or thiophene rings represented by formula (II)

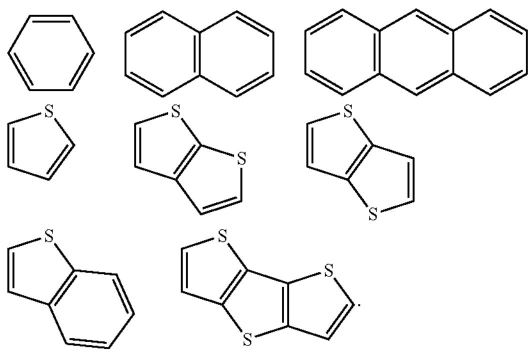

The aromatic hydrocarbons, polycyclic hydrocarbons, heteroaromatic hydrocarbons and polycyclic heteroaromatic hydrocarbons may have substituents such as halogen atom, alkyl, alkoxy, alkylthio and aryl groups in order to improve dissolubility with a solvent, compatibility with a hole transport material and durability when used in a photoelectric conversion device.

Examples of the halogen atoms include fluorine, chlorine, bromine, and iodine.

The alkyl groups may be cycloalkyl groups and include alkyl groups having 1 to 30, preferably 1 to 18 carbon atoms, such as methyl, ethyl, propyl, i-propyl, 2-ethylpropyl, and cyclohexyl groups. The whole or part of hydrogens of the alkyl group may be a group containing an unsaturated bond or a substituent containing an aromatic ring such as phenyl group. The above alkyl groups may be bonded to each other using an amino group. The terminal end of the above alkyl group may be a hydroxyl, thiol, or amino group. Alternatively, the alkyl group may contain an ether bond (—O—) or an ethylene oxide group the number of which repeating unit is 1 to 15, in the middle of the alkyl chain. Furthermore, two substituents may bond to each other at the terminal ends, to be cyclic ether, for example.

Examples of the alkoxy groups include those having 1 to 30, preferably 1 to 18 carbon atoms, such as methoxy, ethoxy, propyloxy, i-propyloxy, butoxy, t-butyloxy, 2-ethylpropyloxy, and cyclohexyloxy groups.

Examples of the alkylthio groups include those having 1 to 30, preferably 1 to 18 carbon atoms, such as methylthio, ethylthio, proprylthio, i-propylthio, butylthio, t-butylthio, 2-ethylpropylthio, and cyclohexylthio groups.

Examples of the aryl groups include those having 6 to 30, preferably 6 to 18 carbon atoms, such as phenyl and naphthyl groups. The whole or part of hydrogens of the aryl group may be substituted with an alkyl group having 1 to 12, preferably 1 to 8 carbon atoms.

Alternatively, monovalent groups derived from oligomers of the above-described compounds may be preferably used for $X_1$ and $X_2$. No particular limitation is imposed on the number of condensation of the aromatic rings as the oligomers, which are preferably 30-mers or less, more preferably 20-mers or less, particularly preferably from 2-mers to 8-mers.

Alkyl, alkoxy, alkoxyalkyl, alkylthio, and alkylthioalkyl groups used as $X_1$ and $X_2$ in formula (I) are preferably the following groups.

The alkyl groups may be cycloalkyl groups and include alkyl groups having 1 to 30, preferably 1 to 18 carbon atoms, such as methyl, ethyl, propyl, i-propyl, 2-ethylpropyl, hexyl, cyclohexyl, heptyl, octyl, nonyl, decyl, undecyl, dodecyl, pentadecyl, hexadecyl, pentadecyl, and octadecyl groups.

The whole or part of hydrogens of the alkyl group may be a group containing an unsaturated bond or a substituent containing an aromatic ring such as phenyl group. The above alkyl groups may be bonded to each other using an amino group. The terminal ends of the above alkyl group may be a hydroxyl, thiol, or amino group. Alternatively, the alkyl group may contain an ether bond (—O—) or an ethylene oxide group the number of which repeating unit is 1 to 15, in the middle of the alkyl chain. Furthermore, two substituents may bond to each other at the terminal ends, to be cyclic ether for example. Further alternatively, aromatic rings are ring-fused.

Examples of the alkoxy groups include those having 1 to 30, preferably 1 to 18 carbon atoms, such as methoxy, ethoxy, propyloxy, i-propyloxy, butoxy, t-butyloxy, 2-ethylpropyloxy, and cyclohexyloxy groups.

The alkoxyalkyl group is represented by $R^1$—O—$R^2$— wherein $R^1$ is an alkyl group having 1 to 30, preferably 1 to 18 carbon atoms and $R^2$ is an alkylene group having 1 to 30, preferably 1 to 18 carbon atoms. Examples of the alkoxyalkyl group include methoxymethyl, ethoxymethyl, methoxyethyl, ethoxyethyl, methoxypropyl, ethoxypropyl, methoxybutyl, ethoxybutyl, methoxypentyl, ethoxypentyl, methoxyhexyl, and ethoxyhexyl groups.

Examples of the alkylthio groups include those having 1 to 30, preferably 1 to 18 carbon atoms, such as methylthio, ethylthio, propylthio, i-propylthio, butylthio, t-butylthio, 2-ethylpropylthio, and cyclohexylthio groups.

The alkylthioalkyl groups are represented by $R^3$—S—$R^4$— wherein $R^3$ is an alkyl group having 1 to 30, preferably 1 to 18 carbon atoms and $R^4$ is an alkylene group having 1 to 30, preferably 1 to 18 carbon atoms. Examples of the alkylthioalkyl group include methylthiomethyl, ethylthiomethyl, methylthioethyl, ethylthioethyl, methylthiopropyl, ethylthiopropyl, methylthiobutyl, ethylthiobutyl, methylthiopentyl, ethylthiopentyl, methylthiohexyl, and ethylthiohexyl groups.

In the methanofullerene derivatives represented by formula (I) of the present invention, $X_1$ is preferably (a) a monovalent group derived from aromatic hydrocarbons, polycyclic aromatic hydrocarbons, heteroaromatic hydrocarbons containing a heteroatom in the skeleton, or polycyclic heteroaromatic hydrocarbons, (b) a monovalent group derived from aromatic hydrocarbons, polycyclic aromatic hydrocarbons, heteroaromatic hydrocarbons containing a heteroatom in the skeleton, or polycyclic heteroaromatic hydrocarbons, having halogen, or an alkyl, alkoxy, alkylthio or aryl group, substituted for at least one of the hydrogen atoms, (c) a monovalent group derived from oligomers of up to 30-mer of aromatic hydrocarbons, polycyclic aromatic hydrocarbons, heteroaromatic hydrocarbons containing a heteroatom in the skeleton, or polycyclic heteroaromatic hydrocarbons, and $X_2$ is preferably (d) a group selected from alkyl, alkoxy, alkoxyalkyl, alkylthio and alkylthioalkyl groups.

No particular limitation is imposed on how many pairs of methine carbon bonding $X_1$ and $X_2$ the methanofullerene derivative has if the purpose of the present invention can be achieved. However, the number of substituent "n" in formula (I) is an integer of preferably 1 to 10, more preferably 1 to 5.

The methanofullerene derivatives represented by formula (I) of the present invention is characterized in that the average value of the $^{13}$C-NMR chemical shift values of $C_2$ and $C_{2'}$ on FL, bonded to $C_1$ bonded to FL, $X_1$ and $X_2$ is 80.10 ppm or greater.

In the present invention, the average value of the chemical shift is hereinafter referred to as "CS value".

$$\text{CS value (ppm)}=[CS(C_2)+CS(C_{2'})]/2$$

CS ($C_2$): $^{13}$C-NMR chemical shift value of carbon $C_2$ (ppm)

CS ($C_{2'}$): $^{13}$C-NMR chemical shift value of carbon $C_{2'}$ (ppm)

In the present invention, $^{13}$C-NMR spectrum is measured as follows.

After 10 to 50 mg of a sample are completely dissolved and homogenized in 1 ml of deuterated chlorohorm in a sample tube for NMR having a diameter of 5 mm, the sample is subjected to the proton decoupling method at room temperature (27° C.) to determine the $^{13}$C-NMR spectrum.

The measurement is carried out under conditions of a flip angle of 90° and a pulse interval of 5T1 or greater (T1 denotes the maximum value of spin-lattice relaxation time of methyl group). It is preferred to carried out the measurement at a cumulated number of 1000 times or more using an NMR apparatus that can provide a $^{13}$C core resonance frequency of 25 MHz or greater in order to increase the determination precision.

In the present invention, the CS value is necessarily 80.10 ppm or greater, preferably 80.20 ppm or greater, more preferably 80.30 ppm or greater. The upper limit of the CS value is 100.00 ppm.

A CS value of smaller than 80.10 ppm is not preferable because it causes the resulting solar cell to be low in open end voltage due to a reduction in electron donating properties from the methine group. A CS value of greater than 100.00 ppm is not preferable for a photoelectric conversion material because it harms significantly the electron accepting properties of $C_{60}$.

Description will be given of an example of a method of synthesizing the methanofullerene derivative of the present invention. However, the present invention is not limited to this method. Tosylhydrazone, which is a precursor of the intended methanofullerene (1a, 3a, 5a, 6a in Examples and 2a and 4a in Comparative Examples below) and fullerene are heat-refluxed in solvents such as o-dichlorobenzene and pyridine at a temperature of 50 to 150° C. for one to 12 hours thereby producing the intended methanofullerene derivative.

A photoelectric conversion device produced using the methanofullerene derivative of the present invention will be described next.

The photoelectric conversion device of the present invention may be a heterojunction type device having a photoelectric conversion layer formed on a substrate by combining the methanofullerene derivative of the present invention that is an electron transport material used as a photoabsorption material with a suitable hole transport material. The heterojunction type electric device exhibits characteristics of a photoelectric conversion device that for example, the methanofullerene derivative and hole transport material generate charge by absorbing light so that the output charge, i.e., current value changes by absorbing light.

The specific structure of the photoelectric conversion device of the present invention may be a structure wherein a transparent electrically conductive substrate, a photoelectric conversion layer of the methanofullerene of the present invention and a hole transport material, and a counter electrode are laminated in this order.

The hole transport material may be a hole transport polymer such as polythiophene, polypyrrole, polyaniline, polyfuran, polypyridine, or polycarbazole. Among these polymers, polythiophene-based hole transport materials are preferably used as hole transport material for the methanofullerene derivative of the present invention.

For the polythiophene, those wherein thiophene or substituted thiophene as a monomer unit is polymerized at the 2- and 5-positions are suitably used. Examples of the substituted thiophene include alkyl-substituted thiophenes and aryl-substituted thiophenes. More specific examples of the thiophene structure include poly(3-methylthiophene), poly(3-butylthiophene), poly(3-hexylthiophene), poly(3-octylthiophene), poly(3-decylthiophene), poly(3-dodecylthiophene), poly(3-phenylthiophene), and poly(3-(p-alkylphenylthiophene). Among these polythiophenes, preferred are those with a high mobility, for example, those polymerized in a sterically regulated manner.

The photoelectric conversion layer may be formed by dissolving the methanofullerene derivative of the present invention and a hole transport material in a solvent to produce a solution and coating the solution on a transparent electrically conductive substrate followed by removal of the solvent.

No particular limitation is imposed on the solvent if it can dissolve both the methanofullerene derivative and hole transport material. Examples of the solvent include benzene, toluene, xylene, chloroform, dichloromethane, tetrahydrofuran, dioxane, carbon tetrachloride, ethylbenzene, chlorobenzene, dichlorobenzene, propylbenzene, ethylene dichloride, and methyl chloride. No particular limitation is imposed on the concentration of the methanofullerene derivative and hole transport material. However, in view of production, the concentration is preferably on the order of 0.1 to 5 percent by mass. If the methanofullerene derivative and hole transport material are unlikely dissolved, they may be stirred and heated.

No particular limitation is imposed on the method of coating the solution dissolving the methanofullerene derivative and hole transport material on a transparent electrically conductive substrate. Examples of the method include casting, spin-coating, spray-coating, and bar-coating. No particular limitation is imposed on the amount of coating. However, the solution is usually coated in an amount of 0.002 to 0.1 ml per $cm^2$ of the substrate. The solvent is then removed thereby forming a photoelectric conversion layer. The solvent may be removed by heating the substrate.

The transparent electrically conductive substrate is usually produced by laminating a transparent electrode layer over a transparent substrate. No particular limitation is imposed on the transparent substrate. The material, thickness, size, and shape of the substrate can be properly selected depending on the purposes. For example, the substrate may be a colored or colorless glass, a wire glass, a glass block, or alternatively be a colored or colorless transparent resin. Specific examples of such a resin include polyesters such as polyethylene terephthalate, polyamides, polysulfones, polyethersulfones, polyether ether ketones, polyphenylene sulfides, polycarbonates, polyimides, polymethylmethacrylates, polystyrenes, cellulose triacetates, and polymethyl pentenes. The term "transparent" used herein denotes a transmissivity of 10 to 100 percent. The substrates used herein are those having a smooth surface at ordinary temperature, which surface may be flat or curved or deformed with stress.

No particular limitation is imposed on the transparent electrically conductive film forming the electrically conductive layer of the transparent electrode. The film may be a metal film of gold, silver, chromium, copper, or tungsten or an electrically conductive film of a metal oxide. Preferable examples of the metal oxide include those produced by doping to tin oxide or zinc oxide a trace amount of a different metal element, such as Indium Tin Oxide (ITO ($In_2O_3$:Sn)), Fluorine doped Tin Oxide (FTO ($SnO_2$:F)), and Aluminum doped Zinc Oxide (AZO (ZnO:Al)). The film thickness is usually from 1 nm to 50 μm, preferably from 10 nm to 10 μm. The surface resistance (resistivity) is suitably selected depending on the usage of the substrate but is usually from 0.01 to 500 Ω/sq, preferably from 0.1 to 50 Ω/sq.

A counter electrode is laminated over the photoelectric conversion layer thereby producing a photoelectric conversion device. The counter electrode may be a metal such as gold, platinum, silver, copper, aluminum, magnesium, lithium, and potassium or a carbon electrode. The counter electrode may be arranged by vacuum deposition, electron beam vacuum deposition, sputtering or a conventional method where metal fine particles dispersed in a solvent is coated, and then the solvent is removed by evaporation. Before forming the counter electrode metal layer, layers of various organic and inorganic materials may be formed so as to improve the adhesion between the photoelectric conversion layer and the counter electrode metal layer and the exciton block properties. No particular limitation is imposed on such materials if it accords with the purposes of the present invention. Examples include films of organics such as phenanthrorine and bathocuproin and those of inorganics such as LiF and TiOx.

The mechanism wherein a methanofullerene derivative and a hole transport material function as a solar cell is described in, for example, "Organic Photovoltaics" (Taylor and Francis) by S. S. Sun and N. S. Sariciftci. Generally, when a film of a mixture of a methanofullerene and a hole transport material is formed, they are phase-separated in nano-scale and form a phase separation structure where they mutually interpenetrate. This structure is referred to as bulk heterojunction. In this structure, the methanofullerene and the hole transport material each generate exciton (electron-hole pair) by light irradiation, and this exciton is charge-separated at the interface of the fullerene derivative and hole transport material thereby generating a free carrier (electron and hole). The resulting free electrons and holes propagate the methanofullerene phase and hole transport phase, which are electron attractive and electron donative, respectively and each reach the respective electrode thereby producing photovoltaic power. During this process, the exciton must diffuse to the interface between the methanofullerene derivative and hole transport material layers to be charge-separated. However, since the exciton has a lifetime (τ), the quantity of the exciton decreases over time after absorbing light. When the length of time (τ) taken till the quantity of exciton decays to 1/e is defined as the lifetime of exciton, the diffusion length thereof is defined as $L_D=(D\times\tau)^{1/2}$ where D is the diffusion constant. Since the exciton needs to be charge-separated to free carriers in order to produce a high efficient solar cell, it is necessary to shorten the duration that the exciton generated by absorbing light diffuse as much as possible. If a structure (domain) resulting from phase-separation of each of the methanofullerene phase and the hole transport phase is too large, the average distance at which the exciton moves to be charge-separated is long, resulting in a reduction in photoelectric conversion characteristics. In order to produce a highly efficient solar cell by allowing the exciton to charge-separate efficiently, compatibility of a methanofullerene with a hole transport material needs to be enhanced such that the phase-separation structures do not become too large.

Compatibility of the methanofullerene derivative and the hole transport material refers to mixing characteristics of the methanofullerene derivative and hole transport material in a solid film state resulting from removal of the solvent after coating. The methanofullerene derivative and hole transport material needs to be adequately phase-separated in nanoscale to achieve high photoelectric conversion characteristics, but if they are poor in compatibility, the phase-separation thereof is extremely large and thus causes the device characteristics to degrade as described above. The compatibility in a solid state can be determined by observing through an atomic force microscope an average domain size, using diffuse characteristics or X-ray analysis such that the image of the phase separation structure can be obtained.

The device characteristics can be evaluated by attaching terminals to the transparent electrode and counter electrode and measuring the change in current value when light is irradiated or not, desirously referring to for example JIS C 8911 to 8919, and JIS C 8931 to 8940.

Alternatively, various sealing treatments may be carried out to improve the durability of a device. No particular limitation is imposed on the method of sealing if it matches with the purposes of the present invention. For example, a device may be sealed with various materials with low gas permeability. A method of sealing to obtain low gas permeability may be carried out by bonding a gas barrier layer such as the above-described substrate materials to a device with an adhesive with low gas permeability thereby enhancing the durability of the device.

EXAMPLES

The present invention will be described in more details with reference to the following examples but is not limited thereto.

Example 1

Methanofullerene derivative 1b (PCP) represented by formula (I) wherein $X_1$ is phenyl, $X_2$ is pentyl, and n=1 was synthesized in the following manner.

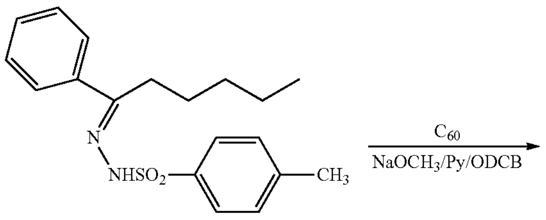

1a

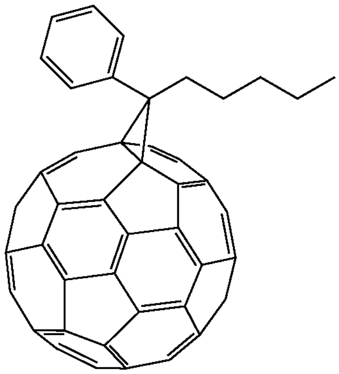

1b

Into a 25 ml pear shape flask were put 300.0 mg of $C_{60}$, which were then dissolved in 9 ml of dried o-dichlorobenzene (ODCB) under an argon atmosphere and subjected to ultrasonic waves for 60 minutes. Into a 50 ml two-neck flask with a Dimroth condenser and a stirrer were put 172 mg of tosylhydrazone is and an equivalent, i.e., 27 mg of sodium methoxide, which were then dissolved in 6 ml of dry pyridine and stirred for 15 minutes, under an argon atmosphere. Thereafter, the ODCB solution of $C_{60}$ was added to the mixture and heated at a temperature of 70° C. for one hour and further heated at a temperature of 100° C. for 4 hours. After the reaction, the ODCB and pyridine were removed by vacuum distillation, and the reminder was separated and refined with a recycle preparative GPC (developing solvent: chloroform) thereby producing 58 mg of brown solid. In 3 ml of ODCB was dissolved the solid, which was then heated at a temperature of 170° C. for 4.5 hours. Thereafter, the solvent was removed by vacuum distillation, and the reminder was separated and refined with a recycle preparative GPC (developing solvent: chloroform) thereby producing 56.6 mg of methanofullerene derivative 1b (15.4% yield). The resulting product was confirmed with a high-performance liquid chromatography (developing solvent: toluene and methanol at 2:3) and identified with $^1$H-NMR, $^{13}$C-NMR, and IR. The CS value of methanofullerene derivative 1b was 80.47 ppm.

[Analysis Data]

IR(KBr) 2961, 2918, 2856, 2328, 1599, 1493, 1426, 1260, 1185, 1092, 1019, 866, 799, 694, 585, 573, 548, 526 $cm^{-1}$;

$^1$H-NMR (300 MHz; $CDCl_3$) δ 7.84 (d, 2H, 6.9 Hz), 7.48-7.35 (m, 3H), 2.80 (t, 2H, 8.1 Hz), 1.82-1.72 (m, 2H), 1.46-1.26 (m, 4H), 0.84 (t, 3H, 7.2 Hz); $^{13}$C-NMR (75 MHz, $CDCl_3$) δ 149.17, 148.30, 146.00, 145.25, 145.20, 145.09, 144.90, 144.85, 144.80, 144.74, 145.56, 144.43, 144.04, 143.85, 143.20, 143.09, 143.06, 143.00, 142.37, 142.29, 142.21, 141.04, 140.78, 138.10, 137.59, 137.37, 132.18, 128.28, 128.06, 80.47, 52.77, 34.33, 31.86, 26.70, 22.63, 14.02

Comparative Example 1

Methanofullerene derivative 2b (PCBM) of formula (I) wherein $X_1$ is phenyl, $X_2$ is 3-(methoxycarbonyl)propyl, and n=1 was synthesized in accordance with the literature entitled with "Journal of American Chemical Society", vol. 60, pp. 532-538, 1995, by J. C. Hummelen, B. W. Knight, F. LePeq, F. Wudl.

The resulting product was confirmed with a high-performance liquid chromatography and identified with $^1$H-NMR, $^{13}$C-NMR, and IR. The CS value of methanofullerene derivative 2b was 79.88 ppm.

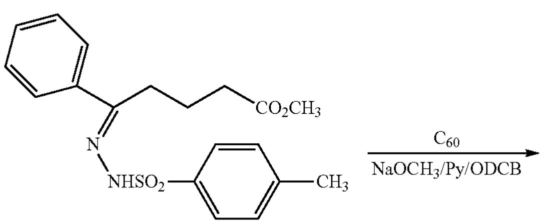

2a

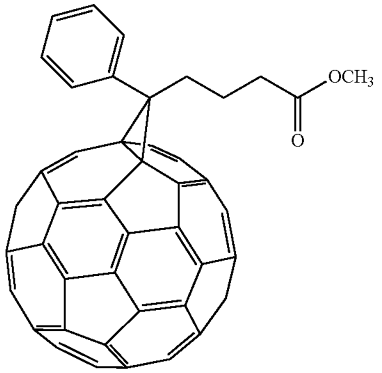

2b

Example 2

Methanofullerene derivative 3b (EThCP) of formula (I) wherein $X_1$ is 5-ethylthiophene-2-yl, $X_2$ is pentyl, and n=1 was synthesized in the following manner.

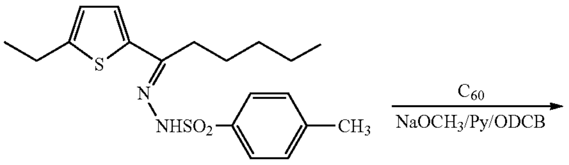

3a

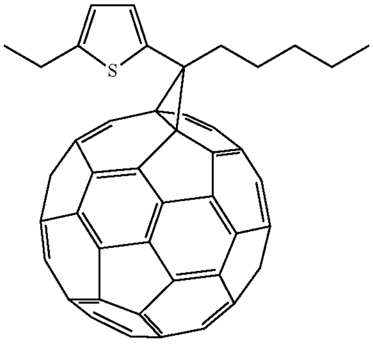

3b

Into a 25 ml pear shape flask were put 100.0 mg of $C_{60}$, which was then dissolved in 3 ml of dry o-dichlorobenzene (ODCB) under an argon atmosphere and subjected to ultrasonic waves for 60 minutes. Into a 50 ml two-neck flask with a Dimroth condenser and a stirrer were put 78.8 mg of tosylhydrazone 3a and an equivalent, i.e., 12.2 mg of sodium methoxide, which were then dissolved in 2 ml of dry pyridine and stirred for 15 minutes, under an argon atmosphere. Thereafter, the ODCB solution of $C_{60}$ was added to the mixture and heated at a temperature of 70° C. for 2 hours and further heated at a temperature of 100° C. for 4 hours. After the reaction, the ODCB and pyridine were removed by vacuum distillation, and the reminder was separated and refined with a recycle preparative GPC (developing solvent: chloroform) thereby producing 44.0 mg of methanofullerene derivative 3b (34.6% yield). The resulting product was confirmed with a high-performance liquid chromatography (developing solvent: toluene and methanol at 2:3) and identified with $^{1}$H-NMR, $^{13}$C-NMR, and IR. The CS value of methanofullerene derivative 3b was 80.73 ppm.

[Analysis Data]

IR(KBr) 2952, 2921, 2852, 2359, 1427, 1375, 1186, 805, 740, 574, 555, 526, 451 $cm^{-1}$;

$^{1}$H-NMR (300 MHz; $CDCl_3$) δ 7.24 (d, 1H, 3.6 Hz), 6.78 (d, 1H, 3.6 Hz), 2.99-2.84 (m, 4H), 1.95-1.85 (m, 2H), 1.55-1.48 (m, 4H), 1.41 (t, 3H, 7.5 Hz), 0.94 (t, 3H, 7.2 Hz);

$^{13}$C-NMR (75 MHz, $CDCl_3$) δ 148.91, 148.18, 145.88, 145.32, 145.28, 145.25, 145.20, 144.90, 144.87, 144.85, 144.73, 144.64, 144.51, 144.19, 143.91, 143.89, 143.19, 143.12, 143.08, 143.00, 142.98, 142.39, 142.32, 142.22, 141.00, 140.77, 138.32, 138.19, 136.74, 131.57, 122.10, 80.73, 47.17, 34.58, 31.70, 26.85, 23.71, 22.67, 15.57, 14.03

Comparative Example 2

Methanofullerene derivative 4b (EThCBM) of formula (I) wherein $X_1$ is 5-ethylthiophene-2-yl, $X_2$ is 3-(methoxycarbonyl)propyl, and n=1 was synthesized in the following manner.

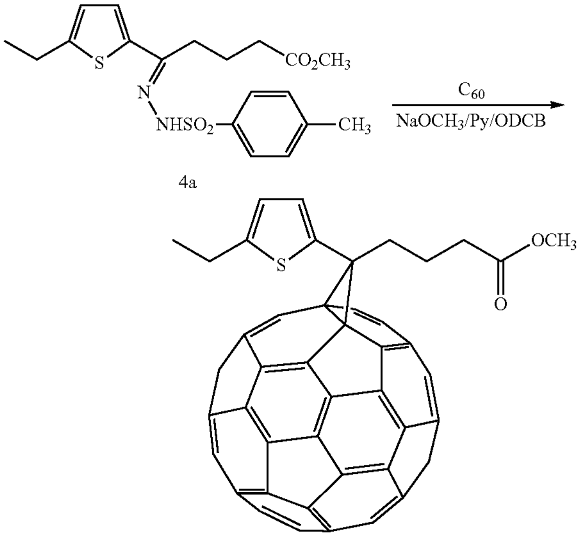

4a

4b

Into a 25 ml pear shape flask were put 50 mg of $C_{60}$, which was then dissolved in 1.5 ml of dry o-dichlorobenzene (ODCB) under an argon atmosphere and subjected to ultrasonic waves for 60 minutes. Into a 50 ml two-neck flask with a Dimroth condenser and a stirrer were put 56.7 mg of tosylhydrazone 4a and 8 mg of sodium methoxide, which were then dissolved in one ml of dry pyridine and stirred for 15 minutes, under an argon atmosphere. Thereafter, the ODCB solution of $C_{60}$ was added from the pear shape flask to the mixture and heated at a temperature of 70° C. for 4 hours and further heated at a temperature of 100° C. for 1.5 hour. The resulting solution was separated and refined with a silica gel column chromatography (developing solvent: toluene) thereby producing 29.5 mg of methanofullerene derivative 4b (EThCBM) (52.2% yield). The resulting product was confirmed with a high-performance liquid chromatography and identified with $^{1}$H-NMR, $^{13}$C-NMR, and IR. The CS value of methanofullerene derivative 4b was 80.08 ppm.

[Analysis Data]

IR(KBr) 2960, 1737 (C═O; s), 1456, 1428, 1376, 1263, 1186, 1170, 983, 885, 806, 741, 572, 562, 525 (s), 445, 432 $cm^{-1}$;

$^{1}$H-NMR (300 MHz; $CDCl_3$) δ 7.27 (d, 1H, 3.60 Hz), 6.78 (d, 1H, 3.60 Hz), 3.69 (s, 3H), 2.99-2.90 (m, 4H), 2.58 (t, 2H, 7.5 Hz), 2.29-2.19 (m, 2H), 1.41 (t, 3H, 7.5 Hz); $^{13}$C-NMR (75 MHz; $CDCl_3$) δ 173.50 (C═O), 148.50, 148.40, 147.65, 145.74, 145.23, 145.20, 145.18, 145.13, 144.81, 144.72, 144.64, 144.57, 144.47, 144.14, 143.82, 143.78, 143.10, 143.04, 143.00, 142.92, 142.90, 142.26, 142.17, 142.13, 142.11, 140.92, 140.70, 138.26, 138.10, 135.97, 131.77 ($\underline{C}$H), 122.20 ($\underline{C}$H), 80.08 (bridge head), 51.66 (O$\underline{C}H_3$), 46.20 (bridge), 33.86 ($\underline{C}H_2$), 33.71 ($\underline{C}H_2$), 23.68 ($\underline{C}H_2$), 22.52 ($\underline{C}H_2$), 15.53 ($\underline{C}H_3$)

Example 3

Methanofullerene derivative 5b (EThCN) of formula (I) wherein $X_1$ is 5-ethylthiophene-2-yl, $X_2$ is nonyl, and n=1 was synthesized in the following manner.

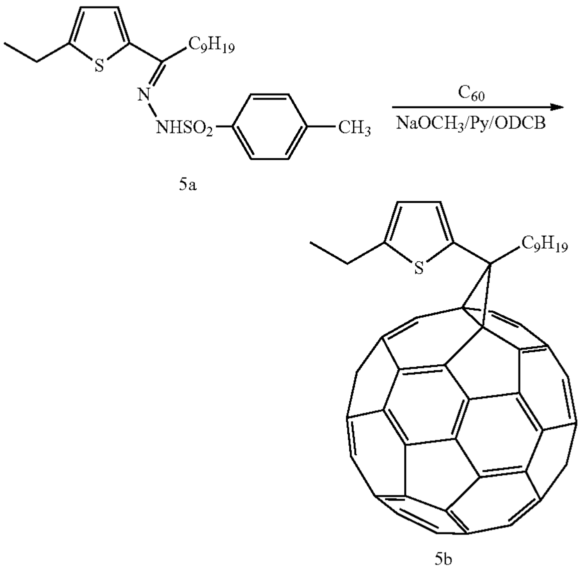

5a

5b

Into a 100 ml pear shape flask were put 1,000 mg of $C_{60}$, which was then dissolved in 30 ml of dry o-dichlorobenzene (ODCB) under an argon atmosphere and subjected to ultrasonic waves for 60 minutes. Into a 100 ml two-neck flask with a Dimroth condenser and a stirrer were put 700 mg of tosylhydrazone 5a and 90 mg of sodium methoxide, which were then dissolved in 20 ml of dry pyridine under an argon atmosphere and stirred for 15 minutes. Thereafter, the ODCB solution of $C_{60}$ was added to the mixture and heated at a temperature of 70° C. for 2 hours and further heated at a temperature of 100° C. for 4 hours. After the reaction, the ODCB and pyridine were removed by vacuum distillation, and the reminder was separated and refined with a recycle preparative GPC (developing solvent: chloroform) thereby producing 473 mg of methanofullerene derivative 5b (35.1% yield). The resulting product was confirmed with a high-performance liquid chromatography (developing solvent: toluene and ethanol at 2:3) and identified with $^{1}$H-NMR, $^{13}$C-NMR, and IR. The CS value of methanofullerene derivative 5b was 80.54 ppm.

[Analysis Data]

IR(KBr) 2918, 2848, 1940, 1457, 1427, 1185, 803, 740, 669, 554, 526 $cm^{-1}$;

$^{1}$H-NMR (300 MHz; $CDCl_3$) δ 7.24 (d, 1H, 3.6 Hz), 6.78 (d, 1H, 3.6 Hz), 2.99-2.84 (m, 4H), 1.94-1.84 (m, 2H), 1.58-1.49 (m, 4H), 1.41 (t, 3H, 7.5 Hz), 1.35-1.20 (m, 8H), 0.88 (t, 3H, 7.2 Hz); $^{13}$C-NMR (75 MHz, $CDCl_3$) δ 148.82, 148.10, 145.81, 145.23, 145.20, 145.17, 145.12, 144.81, 144.77, 144.66, 144.56, 144.43, 144.11, 143.84, 143.82, 143.12, 143.04, 143.00, 142.93, 142.91, 142.31, 142.25, 142.14, 140.92, 140.69, 138.22, 138.12, 136.61, 131.56, 122.03, 80.54, 47.05, 34.49, 31.92, 29.58, 29.47, 29.33, 27.10, 23.70, 22.70, 15.55, 14.14

Example 4

Methanofullerene derivative 6b (EThCHpd) of formula (I) wherein $X_1$ is 5-ethylthiophene-2-yl, $X_2$ is heptadecyl, and n=1 was synthesized in the following manner.

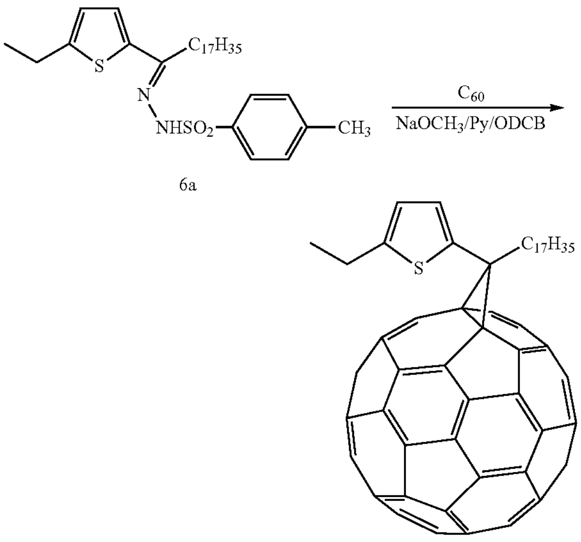

6a

6b

Into a 50 ml pear shape flask were put 500 mg of $C_{60}$, which was then dissolved in 15 ml of dry o-dichlorobenzene (ODCB) under an argon atmosphere and subjected to ultrasonic waves for 60 minutes. Into a 100 ml two-neck flask with a Dimroth condenser and a stirrer were put 440 mg of tosylhydrazone 6a and 45 mg of sodium methoxide, which were then dissolved in 10 ml of dry pyridine and stirred for 15 minutes, under an argon atmosphere. Thereafter, the ODCB solution of $C_{60}$ was added to the mixture and heated at a temperature of 70° C. for 2 hours and further heated at a temperature of 100° C. for 4 hours. After the reaction, the ODCB and pyridine were removed by vacuum distillation, and the reminder was separated and refined with a recycle preparative GPC (developing solvent: chloroform) thereby producing 218 mg of methanofullerene derivative 6b (29.0% yield). The resulting product was confirmed with a high-performance liquid chromatography (developing solvent: toluene and methanol at 2:3) and identified with $^{1}$H-NMR, $^{13}$C-NMR, and IR. The CS value of methanofullerene derivative 6b was 80.53 ppm.

[Analysis Data]

IR(KBr) 2918, 2847, 1716, 1540, 1461, 1427, 1374, 1212, 1185, 803, 718, 525 $cm^{-1}$;

$^{1}$H-NMR (300 MHz; $CDCl_3$) δ 7.24 (d, 1H, 3.6 Hz), 6.78 (d, 1H, 3.6 Hz), 2.99-2.84 (m, 4H), 1.94-1.84 (m, 2H), 1.58-1.49 (m, 4H), 1.41 (t, 3H, 7.5 Hz), 1.32-1.19 (m, 24H), 0.879 (t, 3H, 7.2 Hz); $^{13}$C-NMR (75 MHz, $CDCl_3$) δ 148.81, 148.09, 145.79, 145.22, 145.19, 144.80, 144.64, 144.55, 144.42, 144.10, 143.82, 142.99, 142.92, 142.30, 142.23, 142.13, 140.91, 140.68, 138.10, 136.60, 131.54, 122.02, 80.53, 47.04, 34.45, 31.93, 29.72, 29.60, 29.55, 29.42, 29.37, 27.06, 23.69, 22.70, 15.54, 14.13

Example 5

Baytron P (manufactured by H. C. Stark GmbH) was spin-coated at 5000 rpm (50 s) on a glass substrate having been washed, on which an ITO film with a surface resistance of 15 Ω/sq was formed by sputtering, and then dried at a temperature of 120° C. for 10 minutes. Methanofullerene derivative 1b was mixed with poly(3-hexylthiophene) having a molecular weight of 17,500 (manufactured by Sigma-Aldrich Co. LLC) at a weight ratio of 0.8:1.0, and then dissolved in chlorobenzene such that the concentration of methanofullerene derivative 1b was one percent by weight. As the result, the both materials were completely dissolved and form a homogeneous mixed solution. This mixed solution was spin-coated on the glass substrate at 800 rpm (50 s) thereby forming a photoelectric conversion layer. The ITO-glass substrate with the photoelectric conversion layer was dried under a nitrogen atmosphere over the night, and then 0.5 nm thickness LiF and 100 nm thickness Al were deposited under a vacuum of about $10^{-5}$ torr to form a counter electrode thereby producing a photoelectric conversion device. The resulting device was sealed under an nitrogen atmosphere. For sealing, a glass plate and an epoxy sealant were used. While an artificial sunlight of 100 $mW/cm^2$ was irradiated to the sealed device, the voltage-current characteristics thereof were measured. The maximum efficiency was calculated from the voltage-current characteristics. The result is set forth in Table 1.

Comparative Example 3

A photoelectric conversion device was produced using methanofullerene derivative 2b (PCBM) in the same manner as Example 5 to measure the voltage-current characteristics, from which the maximum efficiency was calculated. The result is set forth in Table 1.

Example 6

A photoelectric conversion device was produced using methanofullerene derivative 3b in the same manner as Example 5 to measure the voltage-current characteristics, from which the maximum efficiency was calculated. The result is set forth in Table 1.

Comparative Example 4

A photoelectric conversion device was produced using methanofullerene derivative 4b in the same manner as Example 5 to measure the voltage-current characteristics, from which the maximum efficiency was calculated. The result is set forth in Table 1.

As set forth in Table 1, Examples 5 and 6 wherein the CS values of the methanofullerenes were larger than 80.10 ppm were higher in open end voltage and also in photoelectric conversion efficiency than Comparative Examples 3 and 4.

TABLE 1

| | methanofullerene | CS value ppm | $J_{sc}$ mA $Cm^{-2}$ | $V_{oc}$ V | FF | η % |
|---|---|---|---|---|---|---|
| Example 5 | PCP (1b) | 80.47 | 6.79 | 0.663 | 0.571 | 2.57 |
| Comparative Example 3 | PCBM (2b) | 79.88 | 6.12 | 0.619 | 0.585 | 2.22 |
| Example 5 | EThCP (3b) | 80.73 | 6.72 | 0.676 | 0.568 | 2.58 |
| Comparative Example 3 | EThCBM (4b) | 80.08 | 6.10 | 0.628 | 0.587 | 2.25 |

INDUSTRIAL APPLICABILITY

The methanofullerene derivative of the present invention is a material applicable as an organic semiconductor material in electronics devices such as organic filed-effect transistors (organic FET) and electroluminescence devices and solar cells and thus has significant industrial values.

The invention claimed is:

1. A methanofullerene derivative selected from the group consisting of:

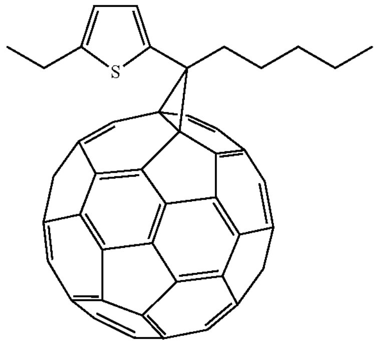

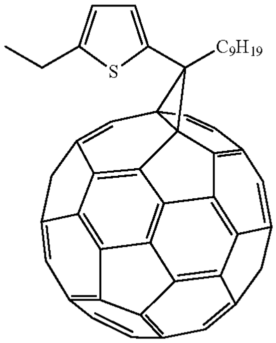

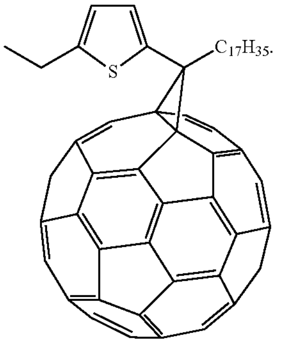

2. A photoelectric conversion device comprising the methanofullerene derivative defined in claim 1 as an electron transport material.

3. The photoelectric conversion device according to claim 2 comprising a conjugated polymer compound containing a thiophene ring as a hole transport material.

* * * * *